United States Patent
Nicholson et al.

(10) Patent No.: US 6,679,887 B2
(45) Date of Patent: Jan. 20, 2004

(54) SURGICAL PROCEDURE FOR IMPLANTING SPINAL FUSION DEVICE

(75) Inventors: James E. Nicholson, Lincoln, MA (US); Scott G. Tromanhauser, Marblehead, MA (US); Dale E. Whipple, East Taunton, MA (US)

(73) Assignee: Cortek, Inc., Dedham, MA (US)

( * ) Notice: Subject to any disclaimer, the term of this patent is extended or adjusted under 35 U.S.C. 154(b) by 31 days.

(21) Appl. No.: 09/871,908

(22) Filed: Jun. 4, 2001

(65) Prior Publication Data

US 2002/0032483 A1 Mar. 14, 2002

Related U.S. Application Data

(63) Continuation-in-part of application No. 09/072,777, filed on May 6, 1998, now Pat. No. 6,241,769.

(51) Int. Cl.[7] ................................................. A61B 17/00
(52) U.S. Cl. ........................ 606/84; 606/61; 623/17.16
(58) Field of Search .............................. 606/60, 61, 99, 606/100, 79, 80, 84, 90

(56) References Cited

U.S. PATENT DOCUMENTS

| | | | | | |
|---|---|---|---|---|---|
| 3,867,728 A | * | 2/1975 | Stubstad et al. | ................... | 3/1 |
| 4,349,921 A | * | 9/1982 | Kuntz | ................................ | 3/1 |
| 5,397,364 A | * | 3/1995 | Kozak et al. | .................. | 623/17 |
| 5,484,437 A | * | 1/1996 | Michelson | .................... | 606/61 |
| 5,522,899 A | * | 6/1996 | Michelson | .................... | 623/17 |
| 5,683,391 A | * | 11/1997 | Boyd | .......................... | 606/61 |
| 5,769,897 A | * | 6/1998 | Harle | .......................... | 623/16 |
| 5,897,593 A | * | 4/1999 | Kohrs et al. | .................. | 623/17 |
| 6,096,080 A | * | 8/2000 | Nicholson et al. | ............. | 623/17 |
| 6,139,551 A | * | 10/2000 | Michelson | ........... | 606/79 |
| 6,261,293 B1 | * | 7/2001 | Nicholson et al. | ............. | 606/82 |
| 6,368,325 B1 | * | 4/2002 | McKinley et al. | ............. | 606/99 |
| 2002/0107571 A1 | * | 8/2002 | Foley | ...................... | 623/17.11 |

* cited by examiner

Primary Examiner—Kevin Shaver
Assistant Examiner—Anuradha Ramana
(74) Attorney, Agent, or Firm—Burns & Levinson LLP; Frederick C. Williams; Yan Lan

(57) ABSTRACT

A spinal implant replaces excised tissue removed during spine surgery. This implant includes fasteners which firmly attach it to vertebrae adjacent to excised tissue so as to transmit tension and torsional loads to and from those vertebrae. The body of the implant has through cavities into which bone growth material is placed during surgery. The body of the implant also has a finite modulus of elasticity in compression so as to share compressive loads with emplaced bone growth material and with new bony growth facilitated by the emplaced material and the load sharing.

2 Claims, 12 Drawing Sheets

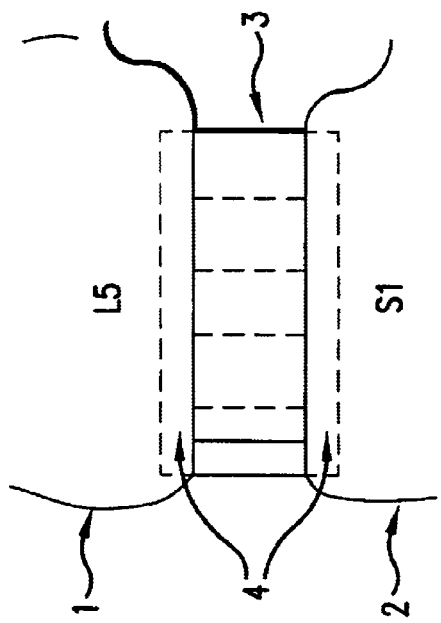
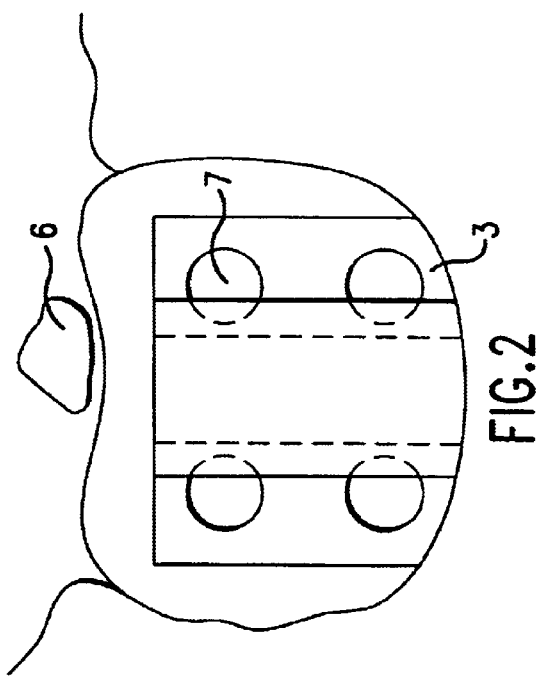
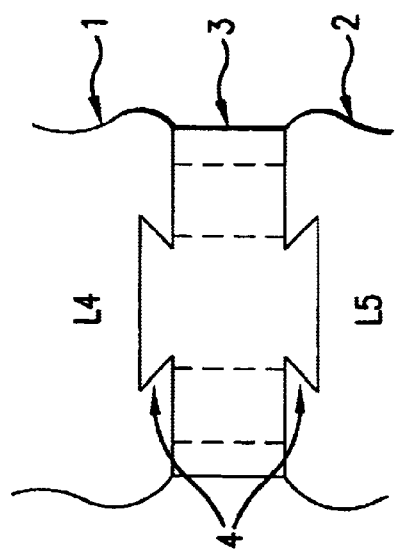

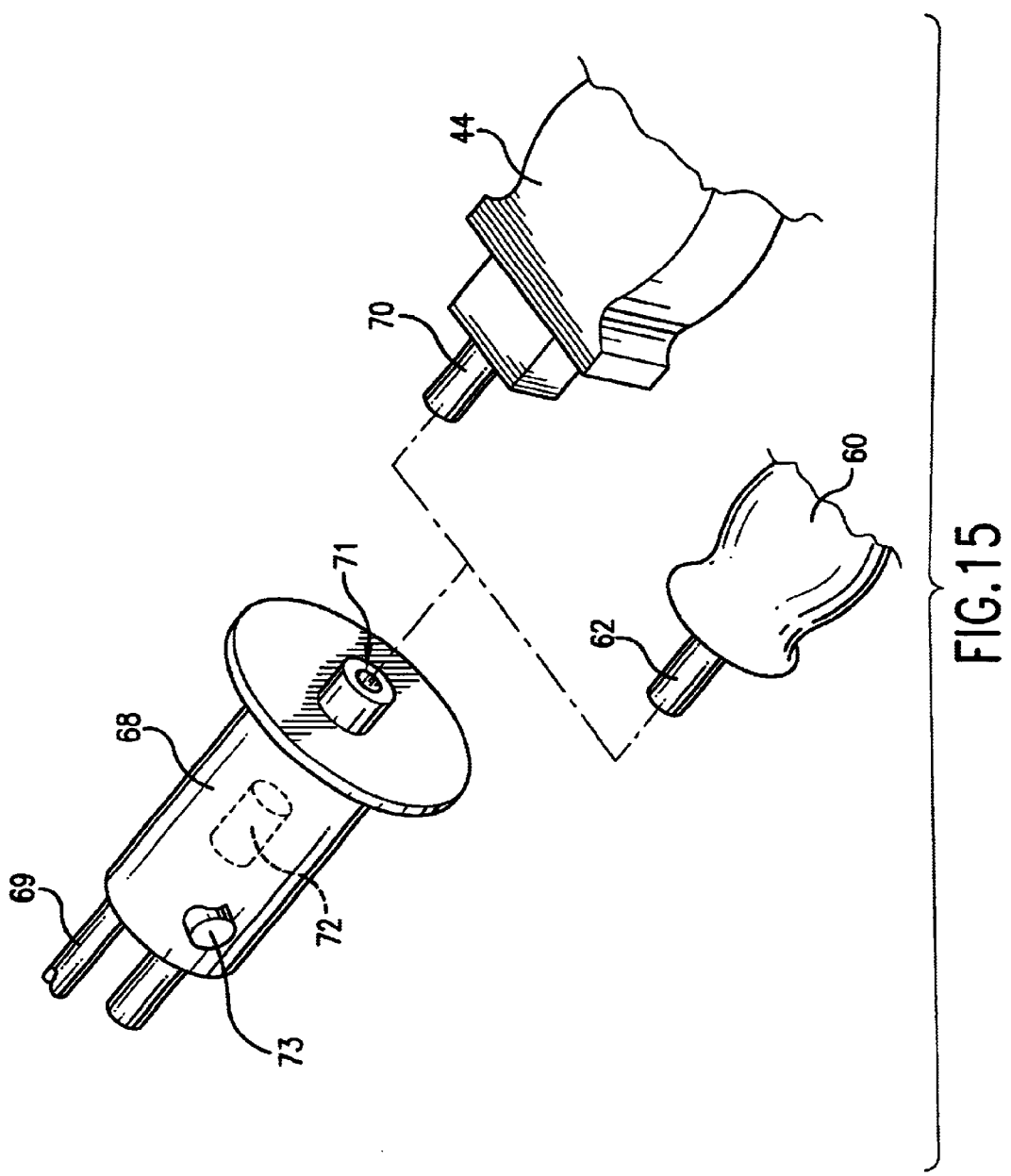

SURGICAL PROCEDURE FOR IMPLANTING SPINAL FUSION DEVICE

This application is a continuation-in-part of U.S. patent application Ser. No. 09/072,777, filed May 6, 1998, issued Jun. 5, 2001 as U.S. Pat. No. 6,241,769 and claims priority based on that application.

BACKGROUND OF INVENTION

1. Field of the Invention

This invention relates generally to the treatment of injured, degenerated, or diseased tissue in the human spine, for example, intervertebral discs and vertebrae themselves. It further relates to the removal of damaged tissue and to the stabilization of the remaining spine by fusion to one another of at least two vertebrae adjacent or nearly adjacent to the space left by the surgical removal of tissue. More particularly, this invention relates to the implantation of devices which can be inserted to take the structural place of removed discs and vertebrae during healing while simultaneously sharing compressive load to facilitate bony fusion by bone growth between adjacent vertebrae to replace permanently the structural contribution of the removed tissue. This invention further relates to the implantation of devices which do not interfere with the natural lordosis of the spinal column. This invention further relates to implants which are radiolucent to permit more accurate diagnostic imaging follow up.

2. Background of the Invention

For many years a treatment, often a treatment of last resort, for serious back problems has been spinal fusion surgery. Disc surgery, for example, typically requires removal of a portion or all of an intervertebral disc. The most common sites for such surgery, namely those locations where body weight most concentrates its load, are the lumbar discs in the L1-2, L2-3, L3-4, L4-5, and L5-S1 intervertebral spaces. In addition, other injuries and conditions, such as tumor of the spine, may require removal not only of the disc but of all or part of one or more vertebrae, creating an even greater need to replace the structural contribution of the removed tissue. Also, a number of degenerative diseases and other conditions such as scoliosis require correction of the relative orientation of vertebrae by surgery and fusion.

In current day practice, a surgeon will use one or more procedures currently known in the art to fuse remaining adjacent spinal vertebrae together in order to replace the structural contribution of the affected segment of the disc-vertebrae system. In general for spinal fusions a significant portion of the intervertebral disk is removed, and if necessary portions of vertebrae, and a stabilizing element, frequently including bone graft material, is packed in the intervertebral space. In parallel with the bone graft material, typically additional external stabilizing instrumentation and devices are applied, in one method a series of pedicle screws and conformable metal rods. The purpose of these devices, among other things, is to prevent shifting and impingement of the vertebrae on the spinal nerve column. These bone graft implants and pedicle screws and rods, however, often do not provide enough stability to restrict relative motion between the two vertebrae while the bone grows together to fuse the adjacent vertebrae.

Results from conventional methods of attempting spinal fusion have been distinctly mixed. For example, the posterior surgical approach to the spine has often been used in the past for conditions such as scoliosis, using Harrington rods and hooks to align and stabilize the spinal column. In recent years many surgeons have adopted anterior fusion because of the drawbacks of the posterior approach, the primary problem being that in the posterior approach the spine surgeon must navigate past the spinal column and its nerve structure. However, results of anterior surgery are variable and uncertain because constraining the vertebrae from this side does not address the loads put on the spine by hyperextension, such as from rocking the body in a backwards direction.

Pedicle screws and rods, always implanted posteriorly, tend to loosen either in the bone or at the screw-rod interface if fusion is not obtained. Fusion rates for posterolateral instrumented fusions range from 50% to 90%. It must be kept in mind that plain x-rays are only 65–70% accurate in determining fusion status and most studies use this inadequate method to determine fusion status, suggesting that the non-union rate may be greater than reported. It is also known that posterior pedicle screw systems do not prevent all motion anteriorly, leading to the risk of fatigue failure of the metal and screw breakage. This continued motion may also lead to persistent pain, despite solid posterior bony fusion, if the disc was the original pain generator. These well documented failures of pedicle screws have given rise to extensive litigation in the United States.

In contrast to the U.S. common practice of using either Interbody Fusion (IBF) devices, implanted from the anterior position, or pedicle screws, implanted posterior, in Europe, spine surgeons use both IBF devices and pedicle screws in combination to achieve stability of the spine. These procedures may be more successful in producing fusion but are far more invasive and costly and have higher morbidity for the patient.

More generally there is a great deal of variability in technique and uncertainty in outcome for the various methods now in use for spinal surgery. For example, Fraser, R. D. points out in "Interbody, Posterior and Combined Fusions," Spine, V20(24S):1675, Dec. 15, 1995, "analysis of the literature does not indicate that one form of fusion is significantly better than another for degenerative conditions of the lumbar spine." Fraser did not have the results of recent studies involving use of metal interbody cage devices. Ray, Charles D. reported the results of the original IDE study involving his Ray Threaded Fusion Cage (Ray-TFC) in Spine V22(6):667, Mar. 15, 1997. Two hundred eight patients had two year follow-up and were reported to have 96% fusion rate with only 40% excellent results and 25% fair or poor results.

There are only two published reports on the use of the BAK Threaded Interbody Fusion Cage. The first, published by Hacker, R. J., Spine V22(6):660 Mar. 15, 1997 compares posterior lumbar interbody fusion using the BAK device to anterior and posterior fusion with allograft bone. Hacker found that patient satisfaction was equivalent but overall costs were less for the BAK. Zucherman reported on the early experience with laparoscopically assisted ALIF with BAK but no outcomes data are presented on these first 17 patients. Kuslich, S. D. presented the results of the multi-center IDE study of 947 patients who had fusions using the BAK device at the 1996 annual meeting of the North American Spine Society in Vancouver. He reported a fusion rate of 90.5% and some degree of functional improvement in 93% of patients with pain eliminated or reduced in 85.6% of patients. The data so far for these threaded cages is scanty at best. It is clear that the results are better than those for posterior fusion with or without pedicle screw instrumentation but further studies are needed. Problems with threaded devices will no doubt come to light as they are used under less controlled circumstances in greater numbers of patients.

John Kostuick, M.D., Chief of Spine surgery at John's Hopkins Hospital, Baltimore, Md. (Private Communication with James Nicholson, 2nd R. Roy Camille Meeting, Paris, France, Jan. 28, 1998) vigorously disagrees that fusion can take place within a metal IBF device which shields the bone from load. Dr. Tromanhauser, one of the inventors, in a series of 30 patients implanted with BAK cages, found that at least 9 patients had continued back pain with x-rays and CT scans that were inconclusive for determining fusion. Surgical exploration of these patients has revealed continued motion and no obvious fusion. All patients were explored at least 6 months after cage implantation, a point at which most surgeons would expect fusion.

Recent unpublished research by Dr. Elsig also indicated that 60% of the cases he reviewed had to be reoperated due to failure 6–8 months after initial surgery. There is therefore recognition and belief, especially among Kostuick Fellows who adhere to the principles of Wolfe's law, that loading the bone during fusion through the implant device connecting the opposing remaining vertebrae would yield superior fusion both in strength and in duration of healing time.

It is also well established from the study of bone growth that a bone which carries load, especially compressive load, tends to grow and become stronger. Existing stabilizing implants, in particular IBF's, do not share any of the compressive load with the new bone growth, in fact possibly shielding new bone growth from load. For example, the BAK cage is promoted as being so strong that a pair of BAK cages will support the full body load. Such shielding is well known to inhibit new bone growth and healing.

The biggest limitation in any method of fusion at the present time is the nature of available devices for bridging the space left by excision of diseased or damaged tissue. In particular, interbody fusion (IBF) devices currently on the market in the United States do not provide stability in all planes of motion. There is very little evidence to support the biomechanical stability of these devices. They are generally stable in compression (forward flexion) unless the bone is osteoporotic, which condition could lead to subsidence of the device into the adjacent vertebral body with loss of disc space height. They may be much less stable in torsion and certainly less so in extension where there is no constraint to motion except by the diseased annulus fibrosus which is kept intact to provide just such constraint. It is doubtful that a degenerative annulus could provide any long term "stiffness" and would most likely exhibit the creep typically expected in such fibro-collagenous structures.

Another problem with conventional fusion devices and with IBF's in particular is difficulty in diagnostic follow-up. In assessing whether or not fusion has taken place between adjacent vertebrae and inside the IBF device, normally plain x-rays including flexion and extension views are obtained. The usual method (Cobb) of measuring motion on these x-rays has a 3 to 5 degree range of error, well beyond the motion that may be present leading to pain. It is impossible to see inside a metal IBF with plain x-rays and conclude anything about fusion status. CT scans with reformatted images are increasingly used because of these shortcomings. Newer software for CT scanners has improved the ability to "see" within cages but the metal artifacts produced by the x-rays are still significant and limit the conclusions that can be drawn. Drs. Tromanhauser and Kant have found virtually no differences in CT scans taken immediately post-op and those taken at a six month follow-up.

Accordingly, there is wide spread recognition among spine surgeons of the need for a flexible radiolucent implant device which would replace removed degenerated tissue and be firmly affixed mechanically to opposing vertebrae. Such a device would dramatically increase the probability of successful fusion because it a) would eliminate or significantly reduce relative movement of the adjacent vertebrae and the intervertebral fixation device in extension and torsion, b) would thereby reduce or eliminate the need for supplemental external fixation, c) by compressive load sharing would stimulate rapid growth of the bone elements packed within the intervertebral device by causing osteoinduction within the bone chips, thereby accelerating fusion, d) would allow confirmation that fusion had taken place using standard CT or possibly plain x-rays, and e) would have the potential to be bioabsorbable, potentially being fabricated from such materials as a D-LPLA polylactide or a remodelable type-two collagen so as to leave in the long term no foreign matter in the intervertebral space. In addition, a flexible implant device can be fabricated in whole or in part from human bone allograft material, which is sterilized and processed, automatically matching or approximately matching the elastic properties of the patient's bone. The success rate of fusion using such an approach is anticipated to exceed the success rate of the IBF devices or the external fusion devices alone and at least equal the combined success rate of the current combination IBF and posterior instrumented technique.

However, there is currently no known method of mechanically affixing an interbody implant device, such as those known in the art as "cages," to adjacent vertebrae. All present IBF devices simply jack open the intervertebral space, relying on the muscle, ligamentous, and annular structures which surround the vertebra to hold the implants in place. The annulus is always degenerative in these cases and could not possibly function in any predictable way and therefore cannot be relied upon to provide adequate motion stability.

Furthermore, prior art cages are filled with bone chips which are shielded from compressive load by the stiff metal cage, preventing natural bone ingrowth through the porous cages because the new bone growth cannot be loaded through the rigid implant. This leads to lack of fusion because the bone, according to Wolfe's law, wants to resorb due to stress shielding by the cages. In an effort to overcome this phenomenon, some manufacturers are adding bone growth factors to the cage and/or the bone graft in an attempt to "fool" the bone into fusing through the cage. However, there is no existing method of sharing compressive loads with bone growth material and new bone growth.

Lordosis, which is a pronounced forward curvature of the lumbar spine, is a factor which needs to be taken into account in designing lumbar implants. It is known in the art that preserving the natural curvature of the lumbar spine requires designing into a new device such as the current invention a modest taper approximately equivalent to the effective angularity of the removed tissue. The restoration of normal anatomy is a basic principle of all orthopedic reconstructive surgery.

Therefore there is a perceived need for a device which simultaneously and reliably attaches mechanically to the bony spinal segments on either side of the removed tissue so as to prevent relative motion in extension (tension) of the spinal segments during healing, provides spaces in which bone growth material can be placed to create or enhance fusion, and enables the new bony growth, and, in a gradually increasing manner if possible, shares the spinal compressive load with the bone growth material and the new growth so as to enhance bone growth and calcification. The needed device will in some instances require a modest taper to preserve natural lumbar spinal lordosis. It will also be extremely useful if a new device minimizes interference with or obscuring of x-ray and CT imaging of the fusing process.

Thus it is an object of the current invention to provide a stabilizing device for insertion in spaces created between vertebrae during spinal surgery. It is a further object to create an implantable device for stabilizing the spine by preventing or severely limiting relative motion between the involved vertebrae in tension (extension) and torsion loading during healing. It is a further object to provide a device which promotes growth of bone between vertebrae adjacent to the space left by the excised material by progressive sharing of the compressive load to the bone graft inserted within the device. It is yet a further object to provide mechanical stability between adjacent vertebrae while bone grows through a lumen in the implant and at the same time not diminish the natural lordosis of the lumbar spine. It is a further object of the invention to provide a device which avoids or minimizes interference with various imaging technologies. It is yet another object of this invention to be capable of being fabricated from human bone allograft material.

SUMMARY OF THE INVENTION

The invention disclosed here is a novel implant designed to achieve the foregoing objects. The design of the new implant for spinal surgery includes the possibility of fabricating the device out of material which is elastic, especially in response to compressive loads, preferably with a compressive elasticity closely matched to that of human bone, preferably the patient's bone. In particular, the design includes the capability to fabricate the device from human bone allograft material. The design is also such that the implant mechanically fastens or locks to adjacent vertebrae and stabilizes the involved vertebrae in tension and in torsion while transmitting a portion of the vertical compressive load to new bone growth associated with the device. This feature of the invention will cause osteoinduction within the bone chips loaded into the implant and will share a sufficient portion of the load with existing bone and with the new bone growth to promote further bone growth and not interfere with bone fusion growth. This invention can be tapered to preserve natural lordosis. This invention also minimizes interference with x-ray imaging by virtue of being fabricated in whole or in part from radiolucent materials.

The implant of this invention joins two vertebrae by means of a mechanical fixation device which is hollow to allow bone growth matter to be added to one or more spaces communicating with the top and bottom surfaces for the purpose of promoting fusion. The attachment portion of the mechanical fixation device is, in a first embodiment, a tongue and groove mechanical fastening arrangement. Other mechanical fasteners commonly used in the woodworking art, such as tack and staple devices, can also be used. The mechanical properties of the device are closely matched to the bone's modulus of elasticity so as to promote osteoinduction and rapid bone growth. The devices are generally transparent to existing radiologic imaging techniques so as to allow follow up confirmation of fusion of the adjacent vertebrae. The implant can also be fabricated from bioabsorbable materials so as to leave no long term foreign matter in the body. Human bone allograft material can also be used as the material from which the implant device is fabricated.

An important aspect in the implant procedure is the preparation of the space to receive the implant and the grooves for the dovetail fasteners. A cutting jig is used which distracts the vertebrae and stabilizes them during preparation and acts as a guide for precise cutting. Special tomes are designed to precisely cut the dovetail and prepare the end plate surface. The tomes have an offset which provides for the implant to be sized to slide through the jig but fit very tightly in the space cut into the vertebrae such as to prevent backout of the implants. Once the cutting jig is in place a x-ray is taken to show that the end of the distraction tangs are clearing the spinal canal. The tomes have depth stops which prevent cutting beyond the distraction tangs.

BRIEF DESCRIPTION OF THE DRAWINGS

FIG. 1A is a frontal view of an implant of this invention placed between lumbar vertebrae.

FIG. 1B is a side view of the same implant.

FIG. 2 is a plan view of the same implant.

FIG. 15 is an isometric view of the driver.

DETAILED DESCRIPTION OF THE PREFERRED EMBODIMENT

Figure 4B:
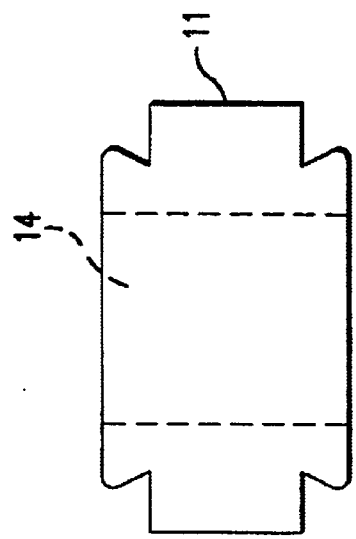
FIG. 4B is a frontal view of a composite implant with inset titanium endplates.

In the currently preferred embodiments, torsional and tensional stability of the spine are provided by fasteners comprising dovetail joints which engage grooves cut during surgery in the vertebrae adjacent to the removed tissue such that the implant and which has large surface contact areas. The dovetails transfer extension and torsional loads between the two vertebrae and the flat contact surface transmits the compressive loads. The device further comprises one or more holes through and/or cavities inside the implant such that the spaces created can be filled with bone graft material which will grow into and attach to the healthy vertebral bone. Optionally in all embodiments tapers to accommodate natural lumbar lordosis can be incorporated as necessary.

The elasticity of the device is selected at a value which promotes sharing of compressive load with bone graft and growth material and new bony growth. In one embodiment, human bone allograft material is used to fabricate the implant. The new fusion bone will gradually share an increasing portion of the compressive loads experienced by the spine because the implant is made of a material, such as a polymer, which has a compressive modulus which works in conjunction with the implant design to closely match the modulus of elasticity of bone during deformation under load. The polymer, or in one embodiment human bone allograft material, has the added advantage of being transparent in x-ray imaging permitting, easy visualization of the fusion process at the vertebrae interface. In a variant of one embodiment, metal retaining clips may be located in the implant surface, both above and below the dovetails, to engage the cortical bone and prevent the implant from migrating out of the intervertebral space. The retainers will generally be metal in order to benchmark x-ray imaging for locking engagement assessment. In yet another variation, locking barbs will be included on the implant top and bottom surfaces to assist in securing the implant to adjacent bony surfaces to minimize pullout.

In a second embodiment of the implant, a plurality of dovetail protrusions, or a compound dovetail protrusion in the approximate layout of a horseshoe may be located on the outboard portions of the implant, thereby utilizing the strength and rigidity of the vertebrae to support the spinal column load. In this case the device would contain a hollow central core which would be filled with bone chip and biological medium to accelerate the fusion in the intervertebral space.

In the first preferred embodiment, as shown in FIGS. 1A and 1B (elevation views), vertebrae L4 and L5 (or vertebrae L5 and S1) are mechanically attached by the implant of this invention 3. The device 3 is held mechanically to the adjacent vertebrae 1 and 2 by tongue and groove, or dovetail, arrangements 4. As shown in FIG. 2 (plan view), the implant 3 is sited so as to provide mechanical support to the spine both in compression and in tension, but not so as to intrude into the space 6 occupied by the spinal nerve bundle. In this preferred embodiment, as shown in FIG. 2, the implant 3 will include penetrations or holes 7 the purpose of which is to contain bone growth material to facilitate bony fusion of the adjacent vertebrae. The implant itself may comprise a variety of presently acceptable biocompatible materials such as Polyphenolsulfone, Polyaryletherketone (PEEK), Polysulfone, Acetal (Delrin), UHMW Polyethylene, and composites of these materials involving high strength carbon fibers or REM glass filaments to add tensile and shear strength. The implant may also be fabricated from human bone allograft material autograft material of bone substitute such as coral or calcium phosphate. The body of the implant may optionally have a modest taper to accommodate the natural lordosis of the lumbar spine.

One possible problem with an implant with dovetail fasteners fabricated from a material such as polysulfone is that torque on one adjacent vertebra relative to the other may place large tension stresses on the angular portions of the dovetail, thereby causing breaking and crazing of the polysulfone. Thus a variation on this embodiment comprises a composite implant fabricated from plastic material such as polysulfone for the body and titanium for endplates bearing the dovetail protrusions.

Figure 4A:
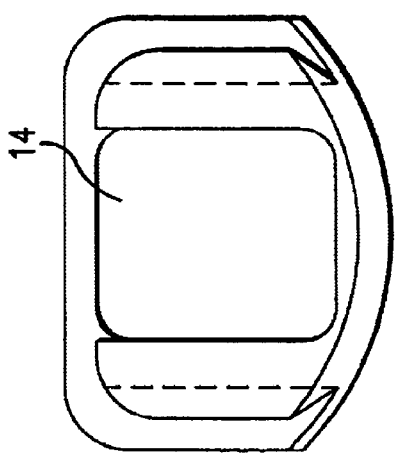
FIG. 4A shows a composite implant with inset titanium endplates in plan view.
Figure 4C:
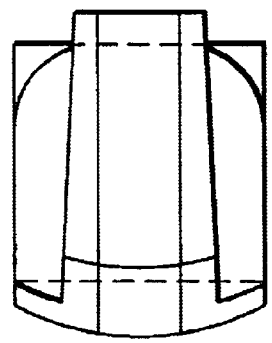
FIG. 4C is a side view of a composite implant with inset titanium endplates.
Figure 3A:
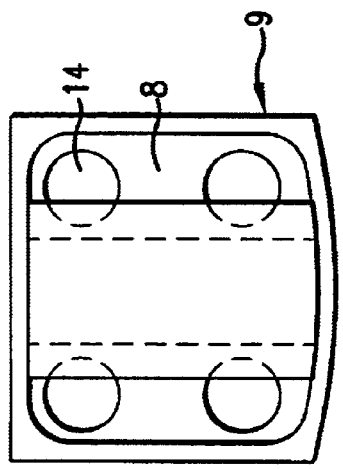
FIG. 3A is a plan view of an implant showing cavities communicating with top and bottom surfaces into which bone growth material is placed.
Figure 3B:
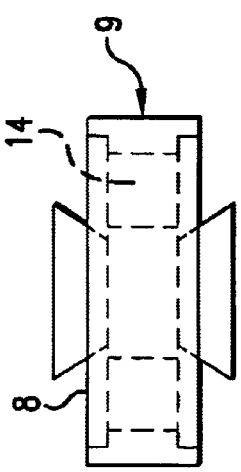
FIG. 3B is a frontal view of the same implant showing cavities.
Figure 3C:
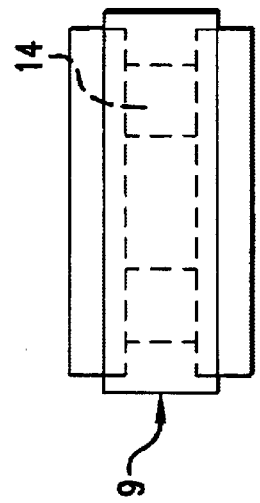
FIG. 3C is a side view of the same implant showing cavities.

FIGS. 3A, 3B, and 3C show one possible arrangement of such a composite structure, with a titanium endplate 8 set into the plastic (and radiolucent) body 9. FIGS. 4A through 4C show a variation on this arrangement with the endplate extending to the shoulders of the plastic body of the implant 11. Both FIGS. 3 and 4 show a variation of this structure, with the titanium endplate 12 set into the plastic body of the implant 9 and 11 in a configuration designed to provide through spaces or cavities 14 in which to place bone growth material. In these latter configurations, the polysulfone body is insert molded into the titanium endplates. The titanium dovetail fasteners possess the tensile strength necessary to avoid fracture or crazing, but the body is still "see through" with respect to X-ray and other methods of visualizing healing progress. In addition, holes in the titanium endplates which are aligned with the bone growth material cavities provides "see through" capability in the vertical direction for assessing new bone growth.

Figure 5:
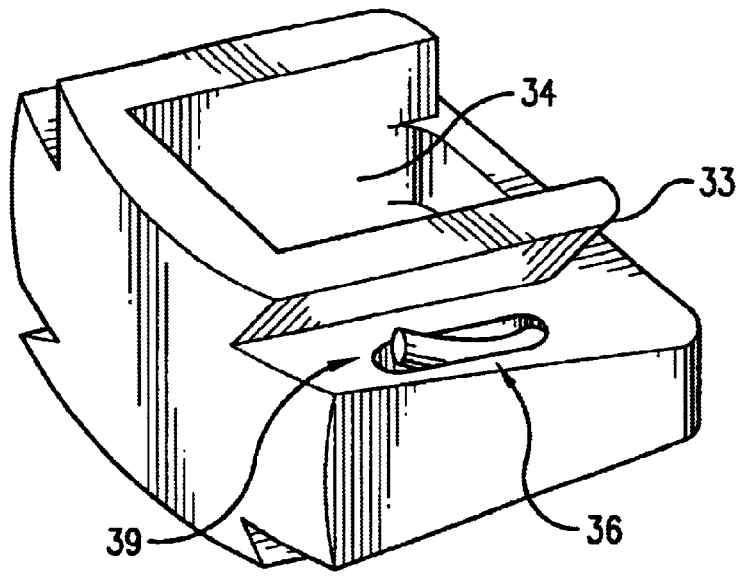
FIG. 5 is an isometric representation of the second embodiment using a horseshoe shaped tongue and groove dovetail fastener and showing the retaining barb.

A second major preferred embodiment, shown in isometric view in FIG. 5, is inserted between two vertebrae, e.g., L4 and L5 or L5 and S1 and mechanically attached by two or more dovetail joints, or by a compound horseshoe shaped dovetail, located on each of the top and bottom surfaces of the implant to the adjacent remaining vertebrae by a composite tongue and groove mechanism similar to but larger than that used to secure the implant of the previous embodiment. In this configuration, the implant comprises either a horseshoe shaped dovetail tongue 33 which in effect creates two dovetail joints per surface toward the outboard ends of the implant top and bottom surfaces or simply two outboard dovetail tongues without the horseshoe top closure. The horseshoe top closure may be substantially curved or it may be substantially straight, with relatively square corners where the dovetail tongue angles back into the body of the vertebra. In a variation on this embodiment, inside the horseshoe shaped dovetail tongue protrusion 33 the body of the implant is hollow, that is, it contains an opening or cavity 34 communicating with both the top surface and the bottom surface into which bone growth material is placed.

Figure 6:
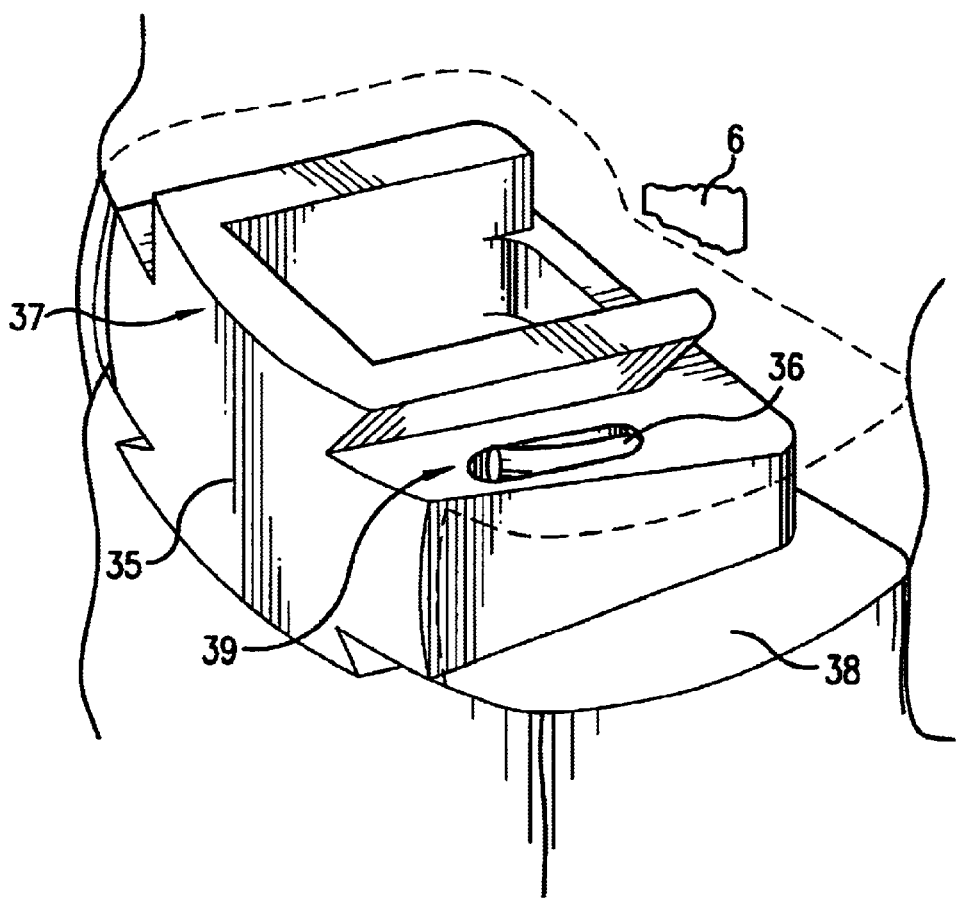
FIG. 6 shows the implant of FIG. 5 inserted between adjacent vertebrae.

In this preferred embodiment, as further shown in the isometric view of FIG. 6, the implant 35 with a relatively squared off horseshoe top closure will have a surface approximately flush with the exterior surface of the adjacent vertebrae and will appear to create one very wide dovetail 37. This embodiment of the implant will also include penetrations or holes in addition to or as an alternative to that shown in FIG. 5, 34, the purpose of which is also to contain bone growth material to facilitate bony fusion of the adjacent vertebrae. As in the prior configuration, the implant 35 is sited so as to provide mechanical support both in compression and in tension to the spinal column, but not so as to intrude into the space 6 occupied by the spinal nerve bundle. The implant in some cases is further inserted inside remaining segments of intervertebral disc tissue 38. As shown in both FIGS. 5 and 6, an optional feature of these embodiments is for the faces of the implant to have locking barbs 36 to retain the implant in place between the remaining vertebrae once it is inserted.

This implant, as in the prior embodiment, may itself comprise a variety of presently acceptable implant materials such as PEEK (Polyesther Esther Ketone), Acetyl (delrin), polysulfone, Ultra High Molecular Weight Polyethylene (UHMW Poly), and composites involving high strength carbon fibers or glass filaments to add tensile and shear strength. Again, human bone allograft material may be used to fabricate this device. This embodiment may also be fabricated with a modest taper to accommodate natural lordosis.

Figure 6A:
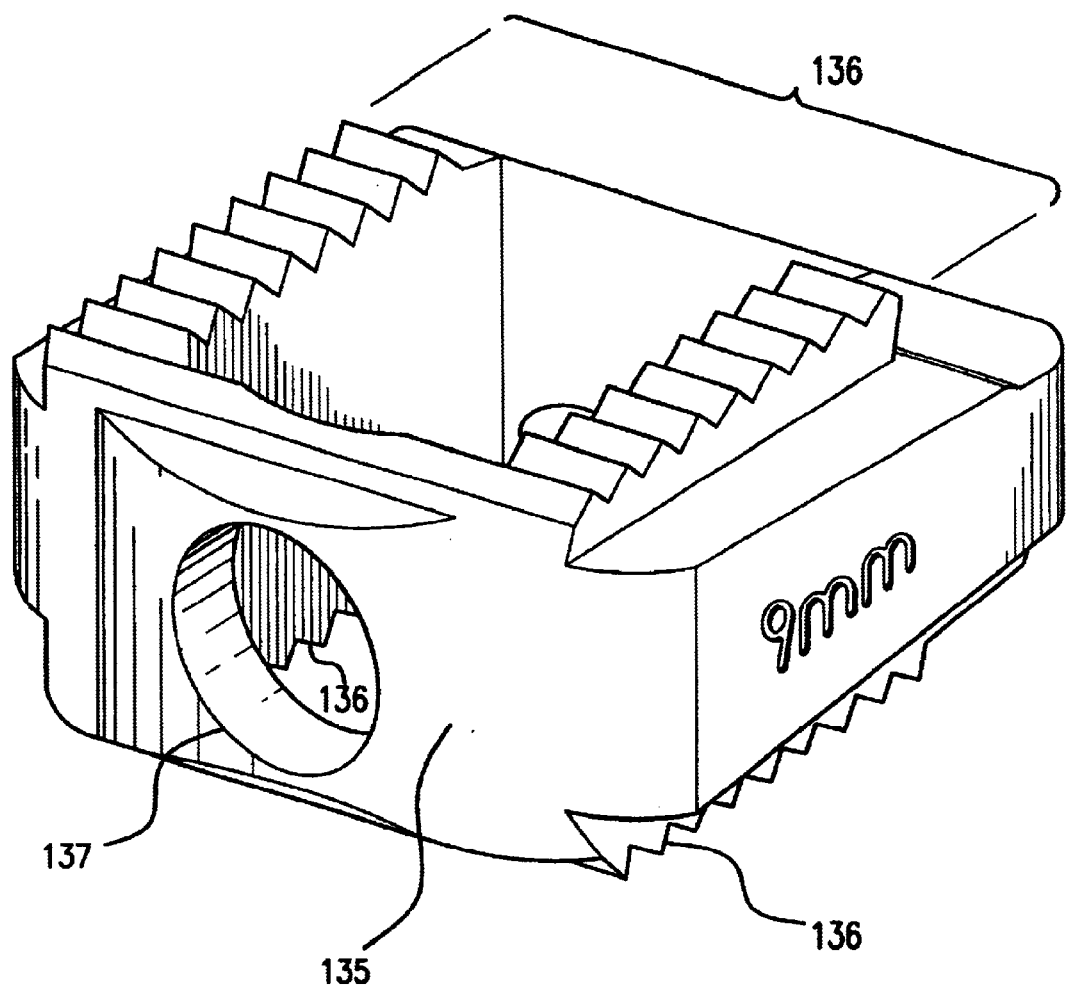
FIG. 6A is an isometric view of a subembodiment with ridges to prevent horizontal motion and a frontal channel to permit addition of bone growth material after implantation.

In a further refinement of this embodiment, the subembodiment shown in FIG. 6A, the locking barbs 36 of FIGS. 5 and 6 are replaced in this subembodiment of the implant 135 with a plurality of ridges 136. The ridges 136 fulfill the same function as the barb, namely preventing the implant from backing out of the intervertebral space as a result of motion of the adjacent vertebrae. A further feature of this subembodiment is the addition of an opening or channel 137 in the curved frontal (anterior when implanted in the patient) surface of the implant 135. The function of this opening or channel is to permit the surgeon to continue to pack additional autograph material into the central cavity of the implant after emplacement in the interverterbral space. The surgeon can also add other material to foster bony growth in the central cavity, such as bone morphogenic protein or bone growth factor, through the channel or opening 137.

Figure 7:
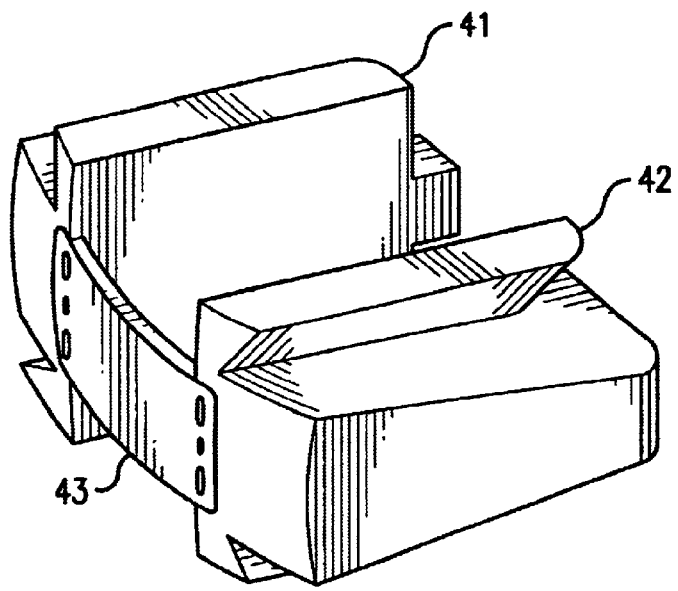
FIG. 7 is an isometric view of a modular implant.

A third preferred embodiment of the lumbar implant, shown in isometric view in FIG. 7, comprises three elements, two modular dovetail halves, 41 and 42, which are inserted between vertebrae L4 and L5 or L5 and S1 and mechanically attached by two dovetail protrusions (similar to those fabricated for the second embodiment) located on the top and bottom of the implant to the adjacent vertebrae by a tongue and groove mechanism similar to but larger than that used to secure previous embodiments of the implant. The two modular dovetail halves are held together by a retainer 43. As in the prior configuration, as shown in the isometric view of FIG. 8, the implant 35 is sited so as to provide mechanical support both in compression and in tension to the spinal column, but not so as to intrude into the space 8 occupied by the spinal nerve bundle.

Figure 8:
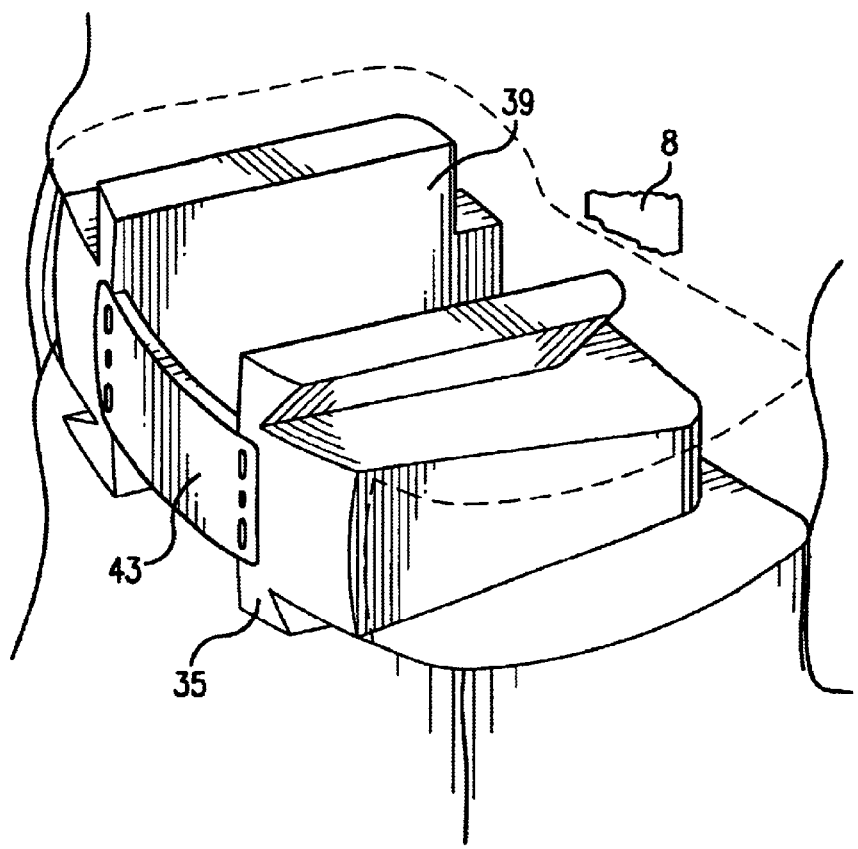
FIG. 8 is an isometric view of the same modular implant with partial depiction of adjacent vertebrae.

In this preferred embodiment, as shown in FIG. 8, the implant 35 will include a cavity 39 the purpose of which is to contain bone growth material to facilitate bony fusion of the adjacent vertebrae. The open space 39 is packed with bone growth material and then capped with a retainer, 43, designed to snap in place to add stability to the implant and to retain the bone growth factor to prevent it from migrating. This implant, as in the prior embodiment, may itself comprise a variety of presently acceptable implant materials such as PEEK (Polyesther Esther Ketone), Acetyl (delrin), polysulphone, Ultra High Molecular Weight polyethylene (UHMW Poly), and composites involving high strength carbon fibers or glass filaments to add tensile and shear strength. Again the modular dovetail halves may be tapered to accommodate lordosis.

Figure 9:
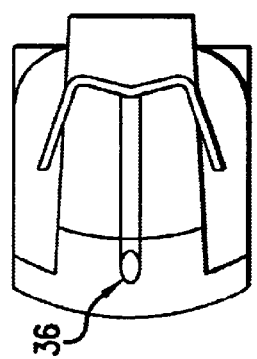
FIG. 9 shows an implant with a retaining barb.

Any of the foregoing embodiments can additionally have a feature shown in FIGS. 5, 6, and 9, namely a retractable barb 36. This barb comprises a spring wire which when deployed engages the adjacent vertebrae to prevent the implant from dislodging. A retraction tool may be inserted into the hole 39 to cause the sigma-shaped barb to retract its probe-like end so that the implant disengages from the adjacent vertebra.

FIGS. 10A through 16B depict the surgical tools used to install the implant. This apparatus comprises a set of unique tools which will accurately cut a dovetail joint in bone for the purpose of inserting an implant which locks adjacent vertebrae together.

Figure 10A:
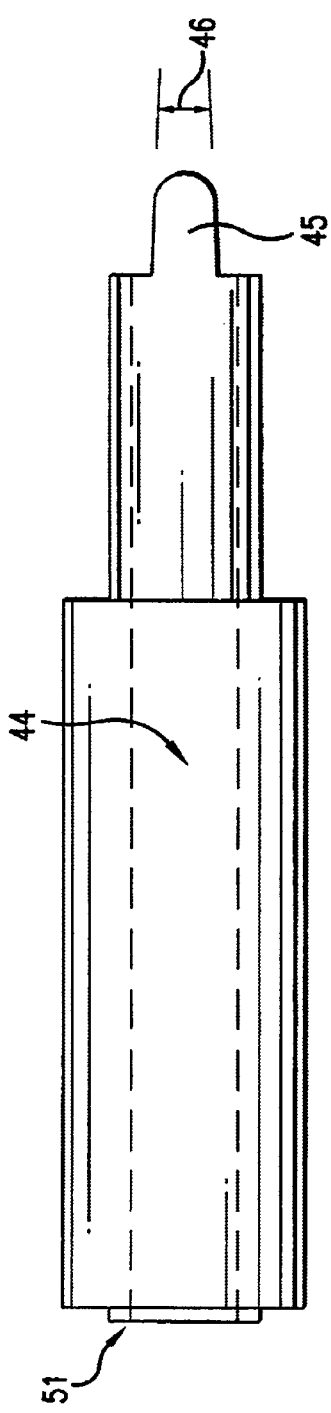
FIGS. 10A and 10B depict the handle of the emplacement instrument for preparation of the implant site.
Figure 10B:
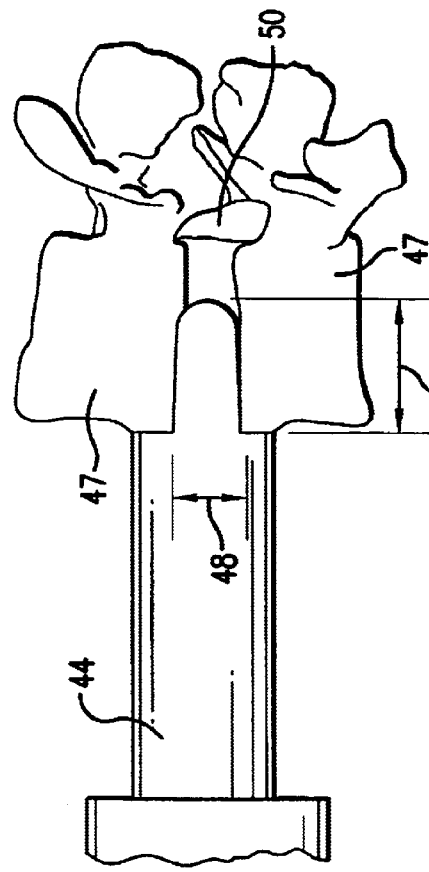

The guide 44, shown in FIGS. 10A and 10B, is a tubular tool with tangs 45 extending from one end. The tangs, tapered 46 to conform to natural lordosis, are inserted between the vertebrae 47 and distract them to a preferred dimension 48, as shown in FIG. 10B. The driver 68, shown in FIG. 15, can be used with a rod extension guide adapter 70, also shown in FIG. 15, to drive the guide 44 into place. This step establishes a fixed reference relative to the two vertebrae 47 and secures the vertebrae from moving. The length 49 of the tangs 45 is consistent with the other tools in the set and establishes the extent 49 to which any tool can penetrate. A lateral x-ray is used to assure that the extent of penetration 49 is safely away from the spinal canal 50. All of the other tools have positive stops which contact the guide depth stop 51 to control the depth of cut.

Figure 11A:
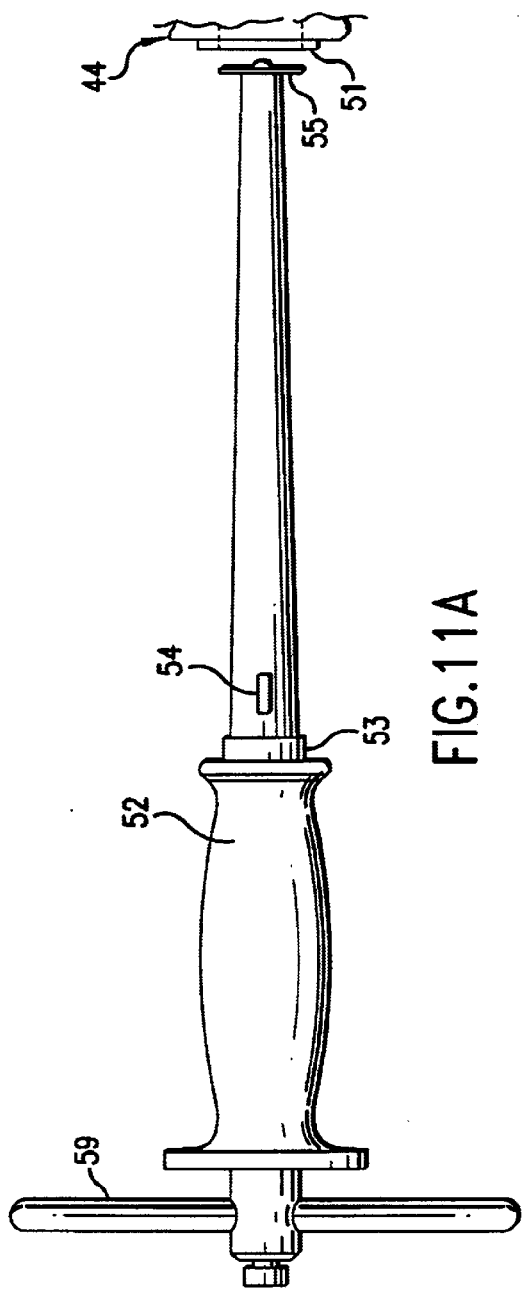
FIGS. 11A and 11B show further details of a cutting tool instrument for preparation of the implant site.
Figure 11B:
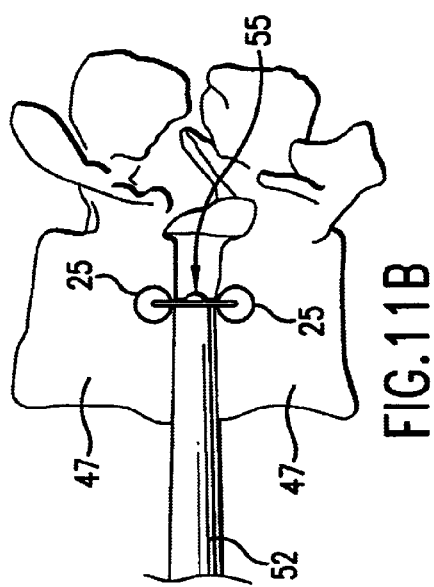
Figure 12B:
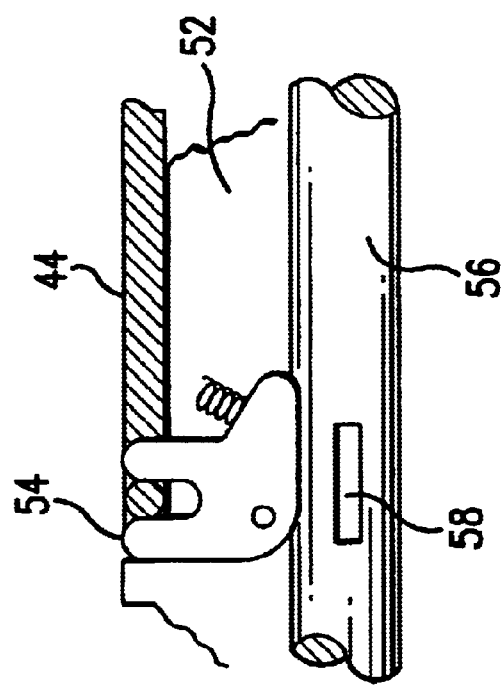
FIGS. 12A and 12B show the operation of the interlock mechanism for the cutting instrument for preparation of the implant site.
Figure 12A:
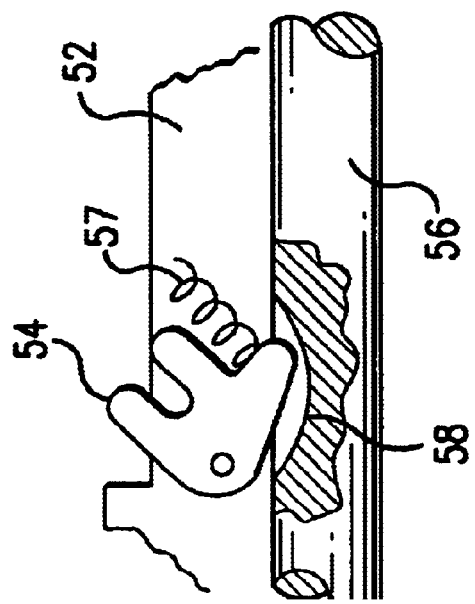

The end cut tool 52, shown in FIGS. 11A and 11B, is inserted into the guide 44 to make an end-cut 52, shown in FIG. 11B, for the dovetail. Once completely inserted to the depth stop 53, a single piece interlock 54, shown in FIGS. 12A and 12B, which prevented rotation of the blade 55 during insertion, is disengaged from the shaft 56 and then prevents withdrawal of the end cut tool 52 from the guide 44. As shown in FIGS. 12A and 12B, the interlock 54 is held by spring 57 such that it engages the slot 58 in the shaft 56, preventing rotation as shown in FIG. 12A. As the end cut tool 52 is inserted into the guide 44 it pushes the interlock 54, rotating it out of the slot 58 in the shaft 56 as shown in FIG. 12B. As the interlock rotates, it engages the guide 44 as shown in FIG. 12B. When the shaft 56 is rotated as shown in FIG. 12B the interlock 54 cannot return to its original position as shown in FIG. 12A, thus securing the end cut tool 52 in the guide 44. The rotation interlock protects the surgeon from the end cut blade 55 and the withdrawal interlock holds the end cut tool 52 in the guide 44 while the blade 55 is exposed. The surgeon rotates the handle 59 one turn, causing the end cut blade 55 to make end-cuts 52 as shown in FIG. 11B, in both vertebrae 47 simultaneously, and returns it to the "zero" position at which the end cut tool 52 can be removed from the guide 44.

Figure 13A:
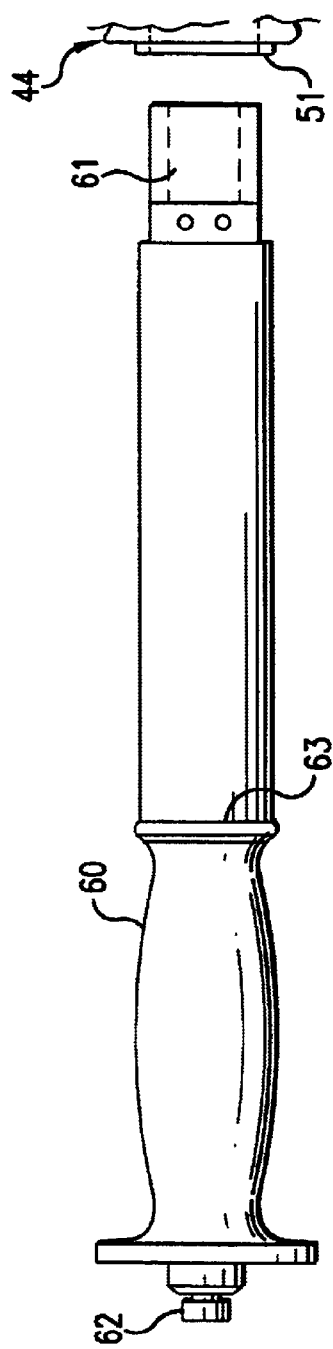
FIGS. 13A, 13B, and 13C show the cutting instrument for preparation of the implant site with dovetail tome deployed.
Figure 13C:
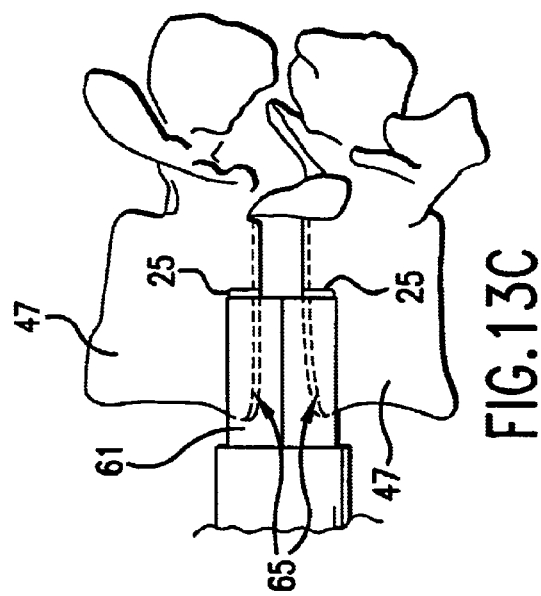
Figure 13B:
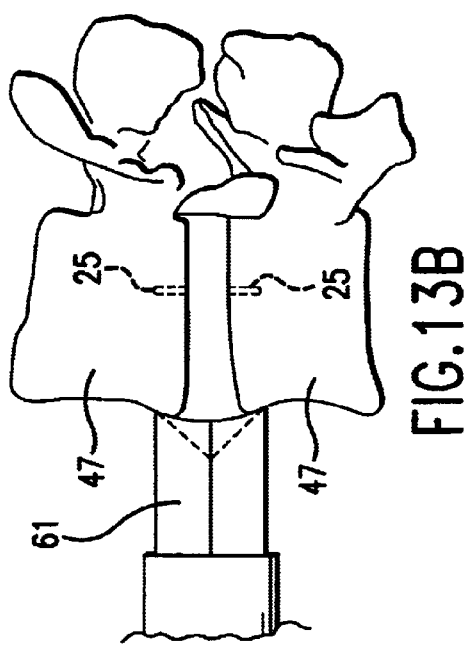
Figure 14B:
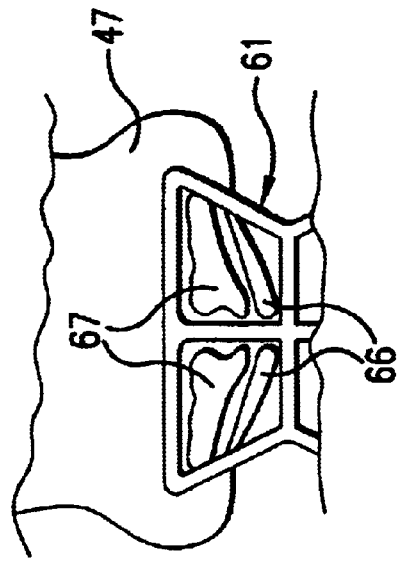
FIGS. 14A and 14B display details of the tome.
Figure 14A:
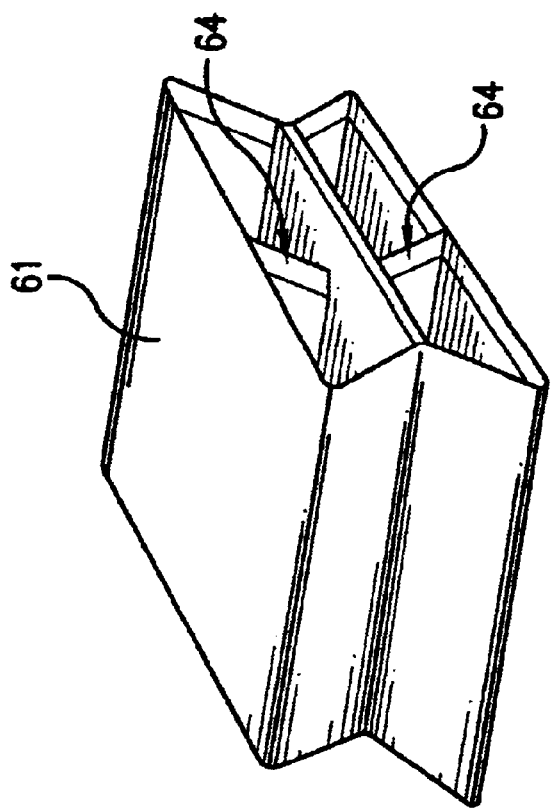
Figure 16A:
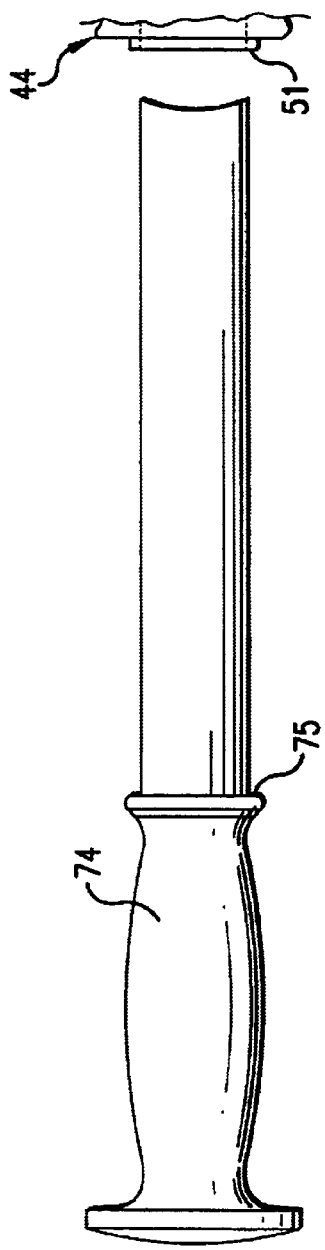
FIGS. 16A and 16B show detail of the placement implement.
Figure 16B:
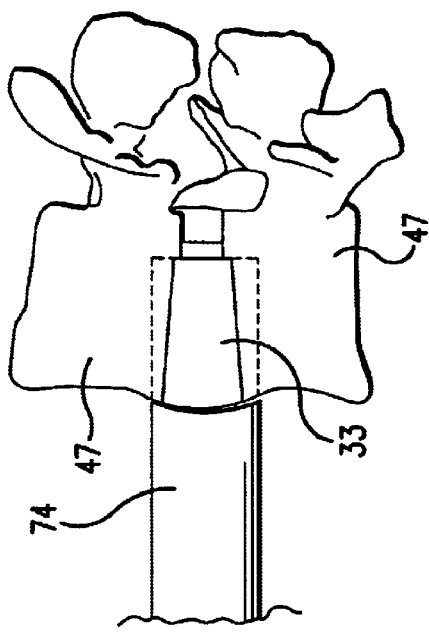

The dovetail tome 60, shown in FIG. 13A, is inserted into the guide 44 to the point where the blade 61 rests against the vertebrae 47. As shown in FIG. 15, the driver 68 is placed on the dovetail tome rod extension 62 and drives the dovetail tome 60, cutting the vertebrae 47, until the depth stop 63 of the dovetail tome contacts the stop 51 on the guide 44, stopping the blade 61 at the end-cut 52, as shown in FIG. 13C. The dovetail tome blade 61, as shown in FIG. 14A, has endplate breakers 64 which split the endplates 65 of the vertebrae (see FIG. 13C) in two 66 as shown in FIG. 14B, preventing them from jamming in the blade and preparing them for later use. The dovetail tome 60 is removed and the bone 67 and the split vertebral end plate 66 contained in the blade 61 is harvested for later use in the implant 33.

As shown in FIG. 15, the driver 68 is a pneumatic tool like a miniature jackhammer. The driver 68 is powered by compressed gas supplied through the input tube 69. The driver 68 receives the rod extension from the guide adapter 70 or the rod extension of dovetail tome 62 into a guide port 71. A piston 72, within the driver 68, repeatedly impacts the guide adapter 70 or the dovetail tome rod extension 62, driving the tool into place. The driver 68 is activated by the finger-actuated valve 73. Control of the force and rate of the impacts is attained by modulating the valve 73. The driver will deliver several thousand small impacts in place of a few massive blows from a hammer.

The implant 33 of FIG. 5 is prepared for insertion by filling the interior portion 34 with harvested bone 67 and the split end plates 66 from the dovetail tome cuts and additional bone and graft stock. The implant 33 is then slid down the guide 44 (FIG. 10) and driven into place by the insertion tool 74, shown in FIGS. 16A and 16B. The insertion tool 74 has a positive stop 75 which contacts the depth stop 51 of the guide 44 and assures correct placement of the implant 33, locking the vertebrae 47.

Implantation Procedure

The first step is to prepare the patient for surgery by placing the patient in a supine position so as to maintain lumbar lordosis. The patient's arms are positioned to accommodate fluoroscopic imaging during the procedure. General endotracheal or nasotracheal anesthesia is established, after which customary surgical prep and draping is accomplished.

The surgeon accesses the retroperitoneal plane anteriorly. In most cases, a standard anterior retroperitoneal approach provides adequate exposure to the anterior aspect of the lumbar spine. Normally the surgeon uses a median incision above the levels to be fused. The rectus muscle is retracted laterally to the left, exposing the posterior rectus sheath superiorly and the peritoneum below the arcuate line.

After separating the peritoneum from the posterior rectus sheath, the surgeon divides the rectus sheath near its insertion at the lateral wall until adequate exposure to the interbody level is accomplished. To access the L3-L4 or L4-L5 disc space, the surgeon mobilizes the left iliac vein and/or vena cava to the right lateral margin of the spine for adequate disc space exposure. To access the L5-S1 disc space, the surgeon must ligate the middle sacral vessels.

To ensure optimal placement of the polymer implant, the surgeon must establish and verify the midline of the cephalad vertebral body at the fusion site. Once the midline is confirmed, it must be marked on the cephalad vertebral body with either cautery or biocompatible dye. The surgeon then performs a complete discectomy, ensuring that the annulotomy is sufficiently wide to accommodate placement of the box guide and subsequent polymer implant.

The surgeon then centers the appropriate size distractor with the midline mark and within the disc space, confirming correct, safe distracter placement by lateral fluoroscopy. The small flanged end of the anvil is placed over the proximal end of the distractor shaft.

The surgeon strikes the large superior surface of the anvil with a mallet, impacting the distractor into the disc space. The distractor is fully seated when the shoulder of the distractor is in contact with the vertebral body or the tip of the distractor is positioned posterior in the disc space.

The surgeon selects a box guide that matches the size of the distractor and places the box guide over the proximal distractor shaft, orienting the "windows" in the box guide to facilitate visualization. After advancing the box guide until the tangs are within the disc space, the surgeon advances the small flanged end of the anvil over the proximal end of the distractor shaft into position at the proximal end of the box guide while maintaining the distractor and box guide positions. Using a mallet to strike the large superior surface of the anvil, the surgeon impacts the box guide tangs into the disc space. The box guide is fully seated within the disc space when the curved shoulders are in contact with the vertebral bodies. Maintaining the position of the box guide, the surgeon removes the anvil and the distractor.

Next the surgeon makes posterior cuts with the end cutter, identified as a HELOTOME™ by Cortek, Inc. An end cut tool makes posterior cuts in adjacent vertebrae. The HELOTOME™ end cut tool is identified as Element 52 in FIGS. 11A and 11B. After ensuring that the selected end cutter handle is in the neutral and locked position, with the T-grip aligned horizontally to the drive shaft, the surgeon, using the grasper, inserts the keyed end of the end cutter shaft through the center hole in the distal surface of the end cutter handle. After advancing until the end cutter is in direct contact with the distal surface of the end cutter handle and in neutral position, parallel to the T-grip, the surgeon inserts the non-flared end of the end cutter locking pin through either of the two side holes at the distal end of the end cutter handle to secure the end cutter in place. The position of the end cutter is adjusted anteriorly using the appropriate box guide spacer.

The technique used to make the posterior cuts varies with the size of the system selected. To make the posterior cuts with an 11 mm or 12 mm system, the surgeon rotates the end cutter handle T-grip clockwise 180 degrees. To make the posterior cuts using a 9 mm or 10 mm system, the surgeon attaches the torque limiting T-handle and rotates the end cutter handle T-grip clockwise 180 degrees. Once the T-grip is returned to the neutral position, the surgeon withdraws the end cutter handle assembly from the box guide.

The next step in the procedure is to make dovetail cuts with the dovetail tome. After assembling the dovetail tome and the dovetail assembly, the surgeon inserts the assembly into the box Guide. Using a mallet to strike the proximal surface of the handle, the surgeon impacts the dovetail tome into the superior and inferior vertebral bodies. When the dovetail tome has fully advanced to the posterior end cut, the vertebral osteotomy is complete.

After removing the dovetail tome assembly from the box guide, the surgeon assesses the intervetebral space with the trial inserter. The autograft material is removed from the dovetail tome. The autograph material ejected from the dovetail tome is broken up and mixed with graft from elsewhere to fill the central cavity of the polymer implant.

The surgeon then inserts the implant through the box guide after assuring that the orientation of the implant is correct, with the rounded surface facing anteriorly. The implant is manually advanced into the prepared intervertebral space until resistance is felt, indicating full implant advancement. The instruments are then removed and the anterior procedure is closed.

The above implant devices contain attachment means which are well known in the woodworking industry, but are not used in Orthopedic Spine Surgery. However, one skilled in the art of intervertebral implants would readily be able to adapt other fastening devices known in the woodworking art to spinal implant devices. It should be readily apparent to anyone skilled in the art that there are several available means to attach bone surfaces to the adjacent implant surfaces, such as causing bone anchors to protrude from the implant surface and impinge and attach the adjacent vertebrae to the implant. Metal staple-like clips can be driven between adjacent vertebrae to attach the edges of the vertebrae. Tack and staple configurations can substitute for the dovetail tongue and groove fasteners. Bone anchors can also be used to attach natural tissue to adjacent vertebrae, creating an artificial ligament which could scar down, thus retaining an artificial implant within the disc space while osteoinduction takes place and the vertebrae fuse.

What is claimed is:

1. A method for preparing two adjacent vertebrae and a disc space therebetween to receive an interlocking spinal fusion implant and for inserting the implant into the disc space, the method comprising the steps of:

performing a discectomy which produces an annulotomy wide enough to accommodate a preselected interlocking intervertebral implant, thereby creating a disc space;

placing either against or within the disc space an appropriate sized distractor having a shaft;

impacting the distractor fully into the disc space;

placing over the proximal end of the distractor shaft the distal end of an appropriately sized box guide having tangs at its distal end and advancing the box guide until the tangs are within the disc space;

removing the distractor through the box guide while maintaining the position of the box guide;

inserting into the box guide a first tome specially configured to make horizontal cuts in the cortical shells of said two adjacent vertebrae;

making horizontal cuts posteriorly in the cortical shells of the two adjacent vertebrae using said first tome;

removing the first tome;

inserting a second tome specially configured to make anterior to posterior cuts in the two adjacent vertebrae of a shape designed to mate intimately with protrusions on the interlocking intervertebral implant, the cuts being made in such fashion that the anterior to posterior cuts end substantially at the posteriorly made horizontal cuts;

removing the second tome from the disc space; and inserting an interlocking intervertebral implant through the box guide into the disc space so that the protrusions on the implant mate intimately with the anterior to posterior cuts.

2. The method of claim 1 in which the anterior to posterior cuts have a dovetail shape and the protrusions on the interlocking intervertebral implant have dovetail shapes which mate with the dovetail shaped anterior to posterior cuts.

* * * * *